US009748085B2

(12) United States Patent
Walker et al.

(10) Patent No.: US 9,748,085 B2
(45) Date of Patent: Aug. 29, 2017

(54) SYSTEMS AND METHODS OF DETECTING AND DEMONSTRATING HEAT DAMAGE TO HAIR VIA EVALUATION OF PEPTIDES (71) Applicant: The Procter & Gamble Company, Cincinnati, OH (US)

(72) Inventors: Ron Walker, Lebanon, OH (US); Yiping Sun, Mason, OH (US); Michael Glenn Davis, Liberty Township, OH (US); Randy Purnell Washington, West Chester, OH (US); Katherine Mae Beglinger, Varysburg, NY (US); Stephanie Lee Davis, Liberty Township, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 14/729,699

(22) Filed: Jun. 3, 2015

(65) Prior Publication Data

US 2015/0364312 A1 Dec. 17, 2015

Related U.S. Application Data (60) Provisional application No. 62/011,275, filed on Jun. 12, 2014.

(51) Int. Cl.
*A61K 38/17* (2006.01)
*C07K 1/00* (2006.01)
*C07K 14/00* (2006.01)
*C07K 16/00* (2006.01)
*C07K 17/00* (2006.01)
*C08H 1/06* (2006.01)
*H01J 49/16* (2006.01)
*G01N 33/68* (2006.01)
*H01J 49/00* (2006.01)

(52) U.S. Cl.
CPC ........ *H01J 49/164* (2013.01); *G01N 33/6851* (2013.01); *H01J 49/0027* (2013.01)

(58) Field of Classification Search
CPC . G01N 33/6851; H01J 49/0027; H01J 49/164
See application file for complete search history.

(56) References Cited

U.S. PATENT DOCUMENTS

| 4,665,741 | A | 5/1987 | Kabacoff | |
|---|---|---|---|---|
| 2011/0281256 | A1* | 11/2011 | Davis | G01N 33/6851 435/4 |
| 2011/0281366 | A1 | 11/2011 | Davis | |
| 2013/0174863 | A1 | 7/2013 | Marsh | |
| 2014/0197309 | A1* | 7/2014 | Davis | G01N 33/6851 250/282 |
| 2015/0182431 | A1 | 7/2015 | Chaudhuri | |
| 2015/0362507 | A1* | 12/2015 | Davis | G01N 33/6851 506/6 |

OTHER PUBLICATIONS

Vazquez Villa et al. Feather keratin hydrolysates obtained from microbial keratinases: effect on hair. BMC Biotechnology 2013. vol. 13, No. 15, pp. 1-11.*
Schwamborn et al. MALDI Imaging Mass SPectrometry—Painting Molecular Pictures. Molecular Oncology, 2010. vol. 4, pp. 529-538.*
Vazquez Villa et al. Feather keratin hydrolysates obtained from microbial keratinases: effect on hair fiber. BMC Biotechnology, 2013. vol. 13, No. 15, pp. 1-11.*
Grosvenor, A.J. "Determination and Validation of Markers for Heat-Induced Damage in Wool Proteins" American J of analytical Chemistry, 2012, 3, 431-436.
Yamashita, S. et al. "A Study of Heat Damage to Hair and How to Indicate Heat Damage" Nippon Keshohin Gijutsusha Kaishi, 2012, vol. 46, 3, 219-223.
Grosvenor, A.J. "Proteomic Characterisation of Hydrothermal Redox Damage" J. Sci Food Agric 2011; 91: 2806-2813.
Grosvenor, A.J. "Isobaric Labeling Approach to the Tracking and Relative Quantitation of Peptide Damage at the Primary Structural Level" J Agric and Food Chem, 2010, 58, 12672-12677.
Kanebo "Specific citrullination causes assembly of a globular S100A3 homotetramer: a putative Ca2+ modulator matures human hair cuticle "J Biological Chemistry, vol. 283, issue 8, pp. 5004-5013 (2008).
Jeon, S.Y. "Comparison of Hair Shaft Damage after UVA and UVB Irradiation" Journal Cosmetic Science (2008), 59(2), 151-156.
Cheng, R. "Evaluation of Hair Damage Degree by Measurement of Cupric Ion Adsorption on Hair" Abstract Riyong Huaxue Gongye (2005), 35(6), 400-402.
Kizawa, K. et al. "Dissimilar Effect of Perming and Bleaching Treatments on Cuticles: Advanced Hair Damage Model Based on Elution and Oxidation of S100A3 Protein" Journal Cosmetic Science., 56, 219-226 Jul./Aug. 2005.
R. Sinclair et al: "The proteomic profile of hair damage", British Journal of Dermatology, vol. 166, Jun. 7, 2012 (Jun. 7, 2012) , pp. 27-32.
Barthelemy Nicolas R et al: "Proteomic tools for the investigation of human hair structural proteins and evidence of weakness sites on hair keratin coil segments" Analytical Biochemistry. vol. 421. No. 1. Feb. 1, 2612 (2612-62-61). pp. 43-55.
International Search Report PCT/US2015/033945; dated Jul. 28, 2015; 13 pages.
Marsh, J.M. et al: "Role of copper in photochemical damage to hair", International Journal of Cosmetic Science, vol. 36, No. 1, Feb. 10, 2014, pp. 32-38.
Won-Soo Lee: "Photoaggravation of Hair Aging", International Journal of Trichology, vol. 1, No. 2, Jul. 1, 2009, pp. 94-99.

(Continued)

*Primary Examiner* — Marcela M Cordero Garcia
(74) *Attorney, Agent, or Firm* — Linda M. Sivik (57) ABSTRACT A method to measure heat damage of keratin fibers comprising eluting a peptide from a hair sample with an aqueous solution; extracting the peptide using a suitable solvent sample; analyzing the peptide samples with MALDI-MS; resulting in peptide results; identifying presence of a marker peptide and identifying the m/z ratio for the peptide.

5 Claims, 5 Drawing Sheets

(56) References Cited

OTHER PUBLICATIONS

Marsh, J.M. et al.: "Advanced hair damage model from ultra-violet radiation in the presence of copper", International Journal of Cosmetic Science, Jun. 9, 2015.
Database UniProt, Feb. 1, 1994, RecName: Full=Protein S100-A3; AltName: Full=Protein S-100E; AltName: Full=S100 calcium-binding protein A3.
Kizawa et al., "Biochemical and Biophysical Research Communications", vol. 299, 2002, pp. 857-862.
Hopfgartner et al., "Chimia", vol. 66, 2012, pp. 335-338.
PCT International Search Report and Written Opinion for PCT/US2015/033943; dated Jul. 27, 2015;.

\* cited by examiner

SYSTEMS AND METHODS OF DETECTING AND DEMONSTRATING HEAT DAMAGE TO HAIR VIA EVALUATION OF PEPTIDES

FIELD OF THE INVENTION

Embodiments of the present disclosure are directed to a process for measuring the heat damage to the hair by the evaluation and identification of extracted peptides.

BACKGROUND OF THE INVENTION

Hair damage through protein loss is a known problem; however, most people have no recognition of the amount of protein loss experienced by their hair, or their level of hair health in general. Protein loss may be caused by everyday occurrences and environmental factors such as UV ray exposure, bleaching, coloring, perming, straightening, heat, mechanical manipulation, and salt water contact.

Proper hair architecture at the molecular level is an important characteristic of hair that has a healthy look, shine and feel. The hair comprises mostly protein and is not regenerative after it exits the scalp. Therefore, it is valuable to have products which protect the overall protein integrity of the hair. Thus, protection of the hair shaft on the protein and fiber level is important to ensure hair has a healthy look.

Identifying the peptide extracted from the hair and correlating the type of peptide with a type of hair damage 1) enables a correct identification of the type of damage to the hair, and 2) may provide the information necessary to design products which either prevent the damage, or in the case of heat or other treatments do not generate the damage. Additionally, it is also valuable to identify particular types of hair disease. Hair of individuals with hair diseases, do not react to damage and/or treatments in the same way as normal hair. Therefore, it may be possible to indicate what type of hair disease is present based upon the response of the hair at a protein level to a particular type of damage.

Heat Damage Effects

It is known that hair is a keratin-based peptide, and like most peptides it is susceptible to thermal degradation. As hair is exposed to increasing temperatures near or above its denaturation temperature via blow dryers, flat iron or curling irons, the peptides begin to degrade and the disulfide bonds begin to decouple. This structural degradation leads to a weakened hair fiber that is more susceptible to breakage and mechanical damage. Further, as hair is continually exposed the repeated heat treatments and high temperatures this degradation is further exacerbated.

Also, as the peptide is identified, products which utilize the available bonds that result from the peptide loss, in particular products specialized for specific damage types, can be produced.

SUMMARY OF THE INVENTION

The present disclosure relates generally to systems and methods for detecting heat hair damage by correlating peptides extracted from the hair to a type of hair damage.

An embodiment of the present invention is directed to a method to measure heat damage of keratin fibers comprising eluting a peptide from a hair sample with an aqueous solution; extracting the peptide using a suitable solvent sample; analyzing the peptide samples with MALDI-MS; resulting in peptide results; identifying presence of a marker peptide and identifying the m/z ratio for the peptide.

A further embodiment of the present invention is directed to a method to identify a treatment for heat damage of keratin fibers comprising applying a treatment composition to a hair sample A and apply no treatment composition to a hair sample B; applying heat to hair sample A and hair sample B; eluting a peptide from hair samples with an aqueous solution; extracting the peptides using a suitable solvent sample; identifying or measuring the marker peptide by identifying the unique modification patterns which exist in sample wherein the MALDI-MS peptide results in a peptide wherein Sample A has a decrease in peptide compared to Sample B.

DETAILED DESCRIPTION OF THE INVENTION

As used herein, "hair" means keratinous fibers of the human or animal origin, such as hairs on the head or eyelashes. Furthermore, as used herein, the term "keratinous peptide" is understood to mean those peptides present in hair. As used herein, the term "protein" means the amino acids and larger proteins that are damaged and broken off the keratinous protein structure and held within the hair structure by electrostatic interactions, weak hydrogen bonding matrix proteins and lipids, or any other force that does not include incorporation in the keratinous protein structure.

As used herein "marker peptide" means the peptide which has been correlated to a particular type of hair damage and/or damaging treatment.

As used herein, "elutes," "eluting," and the like means removing peptides from hair via contacting hair with an aqueous solution without the addition of any reduction or extraction agents, thereby yielding no modification of the keratinous peptide structure and no breaking or reduction of chemical bonds present in the hair sample other than electrostatic interactions, weak hydrogen bonding matrix peptides and lipids, or any other force that does not include incorporation in the keratinous peptide structure.

As used herein, "elutable" means peptide present in the hair sample that may be removed from the hair structure in an aqueous solution without the addition of any reduction or extraction agents. Furthermore, "elutable" means peptides that may be carried out of the hair structure in an aqueous solution consisting essentially of water without the breaking or reduction of chemical bonds present in the keratinous peptide structure other than electrostatic interactions, weak hydrogen bonding matrix peptides and lipids, or any other force that does not include incorporation in the keratinous peptide structure.

As used herein, "heat damage" means damage caused to the hair as a consequence of being exposed to heat treatment. Heat exposure may occur upon treatment with non-limiting examples including styling appliances such as flat irons, curling irons, blow dryers including portable or salon stationary dryers, and heat rollers and the like. Heat damage may occur at an appliance temperature of about 150 F or higher with multiple treatments, or single treatments at an appliance temperature of greater than about 250 F. Typically, heat damage may occur when the hair temperature reaches denaturation temperature, which may be in the range of about 260 F to about 300 F or above, depending on the condition of the hair, non-limiting condition examples such as virgin, bleached and sun-damaged hair.

A method has been developed for detecting and demonstrating hair damage by utilizing an aqueous solution to extract peptides from the hair without modifying the keratinous peptide structure. Once the peptides are extracted from the hair, the peptides are analyzed. From the analysis of the peptides it is possible to identify the type of damage that has been done to the hair, in particular it is possible to determine the source of the damage to the hair. One such specific marker peptide includes those marker peptides generated when the hair is exposed to heat treatments. A hair sample can be tested, the peptides extracted, and the resulting peptides tested using an antibody based detection, and/or a mass spectrometry technique. In one embodiment the peptides are evaluated using the Matrix Assisted Laser Desorption Ionization ("MALDI"), also known as the MALDI Mass Spectrometry "MALDI-MS". This technique is a soft ionization technique used in mass spectrometry. MALDI-MS can be used for the analysis of biomolecules such as peptides and peptides and large organic molecules such as polymers. In MALDI, the analyte is first co-crystallized with a UV absorbing matrix such as α-cyano-4-hydroxycinnamic acid (CHCA), then subjected to pulse laser (YAG or nitrogen laser) radiation. This causes the vaporization/desorption of the analyte/matrix crystals and produces ions which are transmitted into a mass analyzer for detection. In MALDI-TOF, a time-of-flight mass analyzer is used. MALDI-TOF Data can be acquired in MS mode to generate molecular weight information (e.g., a peptide) and in MS/MS mode (e.g., a peptide sequence/structure information). Typical MALDI mass spectrum acquisition takes less than a minute so it can be used for fast screening of molecular species in samples of interest. Changes and molecular makers can be detected by comparing the mass spectra acquired in samples treated under different conditions such as virgin hair vs. heat treated hair.

MALDI-MS can be performed either with or without enzymatic digestion of peptides. The peptide test results are then compared to a library of known marker peptides to identify what type of hair damage, and in some situations, what is the original source of damage to the hair i.e. bleach. This enables a "fingerprinting" of damage; meaning that if a hair sample is tested and the results include certain marker peptides, then the hair sample has been damaged by a particular source.

Additional methods for evaluating the peptides include, but are not limited to, liquid chromatography-electrospray mass spectrometry, antibodies against the peptides could be generated and an ELISA assay could be developed.

Further an iTRAQ method (Isobaric Tags for Relative and Absolute Quantitation) method, reagents available through AB-Sciex, Framingham, Mass.) can be used to establish covalent amine linkage of an isobaric tag to each lysine side chain and free N-terminal group of a peptide. This allows for multiple samples to be run simultaneously through the MALDI MS. Running multiple samples through the MALDI-MS simultaneously minimizes variations in the test data due to test variability.

Furthermore, in an embodiment of the present invention, MALDI-Imaging mass spectrometry can be used to map chemical species directly on surfaces like hair. Peptide fragments on damaged hair can be directly detected and visualized on hair fibers. The marker peptide intensity in a MALDI image that is acquired in the same data acquisition can be compared. For example, single hair fibers from virgin, bleach or UV exposure can be mounted directly on a MALDI plate using a piece of double-sided, conductive adhesive tape. After applying a MALDI matrix like α-cyano-4-hydroxycinnamic acid (CHCA), the hair fiber surface can be analyzed in the imaging mode by rastering the laser beam across the area. Data acquired in the MALDI-Imaging mode can be processed using an imaging software such as Biomap. The ion intensity map on a specific damage marker present on hair fiber surface can be generated for visual comparison.

A library of these marker peptides can be generated by damaging swatches of hair with a variety of different compositions or treatments and then analyzing the resulting peptides in comparison with a similar swatch of hair which has not been damaged. Marker peptides can be identified by the MALDI-MS, as it is believed the same marker peptide results will be found based upon the type of damage that the hair has experienced. This means that the marker peptide is indicative of a type or source of hair damage under certain treatments. Hair damage by heat treatments results in particular marker peptides, hair damaged by bleach results in other particular marker peptides.

Additionally, this method can also be used to indicate whether an individual's hair has a normal response to treatments. For example if an individual has a particular hair disease, a hair sample from this individual may not generate the same marker peptide as would a person who has a "normal" response. A person with a hair disease may generate additional, less and/or even different marker peptides than would be indicated by a normal response. A library of hair disease responses could also be created similar to that of the marker peptide for damage as described above. Therefore, a test for this hair disease could include exposing an individual's hair to a particular damaging treatment and then identifying the hair disease by the marker peptides that are generated from the damaging treatment.

In one embodiment of this hair peptide loss test method the soluble and insoluble peptides are analyzed separately. Analyzing the soluble and insoluble peptides separately can result in higher sensitivity of peptide detection. Additionally, analyzing these peptides separately may further refine the determination of the location of the damage to the hair. To measure the soluble and insoluble peptides separately, after removal of the hair fibers the sample the in water can be centrifuged or the insoluble portion can be left to settle out from the soluble portion.

EXAMPLE A

1) Bleach Procedure
  1. Preparation: Hair Swatches: 4 g×10 inches virgin curly swatches are used.
  2. Bleach: Bleach procedure is carried out in a fume hood. To prepare the bleaching solution, mix the bleaching solution for 1 min. to get well-homogenized solution using the following formula:

| Chemical | Wt. % |
| --- | --- |
| Distilled Water | 65.00 |
| Tetra sodium EDTA | 0.20 |
| 28% NH$_4$OH | 7.15 |
| Acetic Acid (99.7%) | 0.50 |
| 30% H$_2$O$_2$ | 20.00 |
| Distilled Water | 7.16 |

Figure 1:
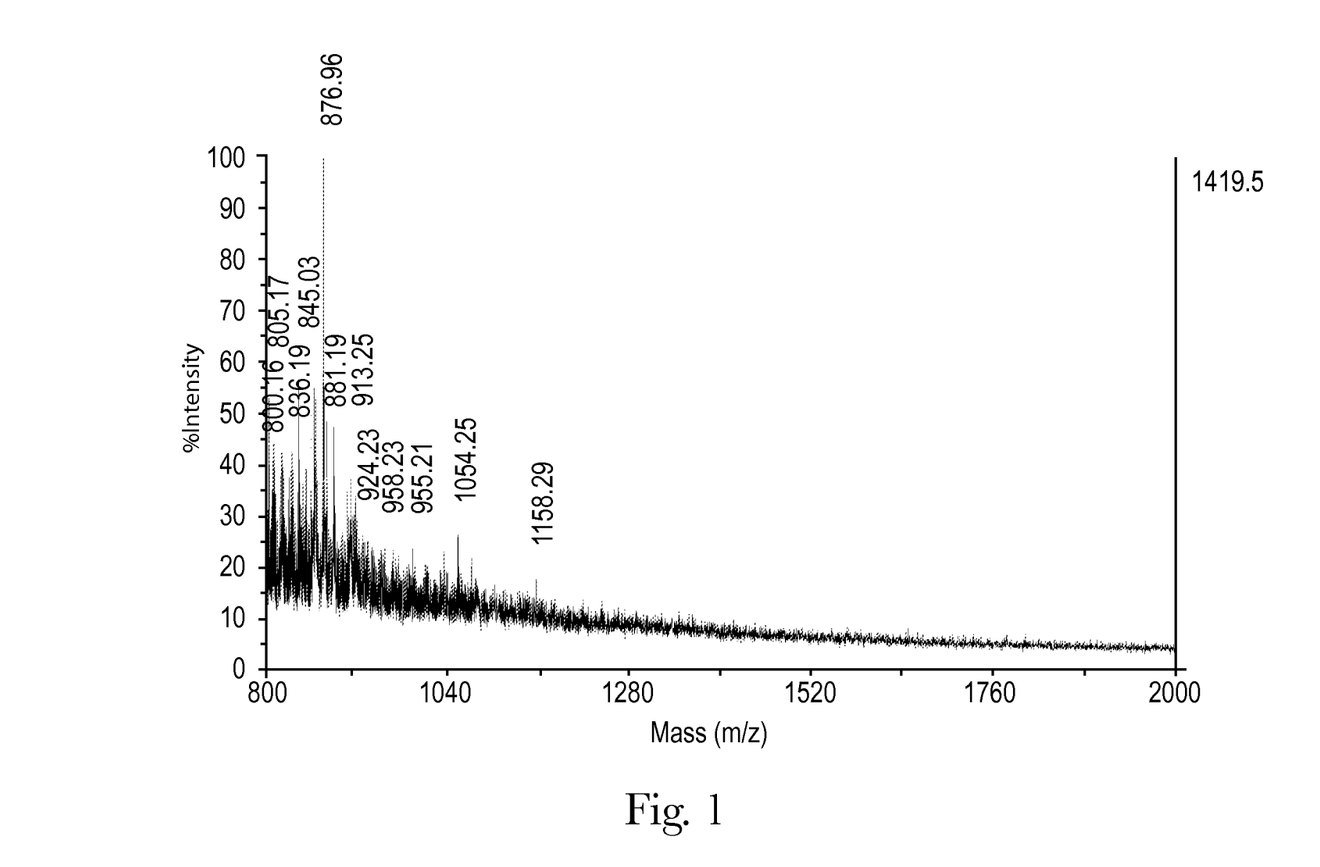
FIG. 1. MALDI mass spectrum of extracts from virgin hair samples without heat treatment.
Figure 2:
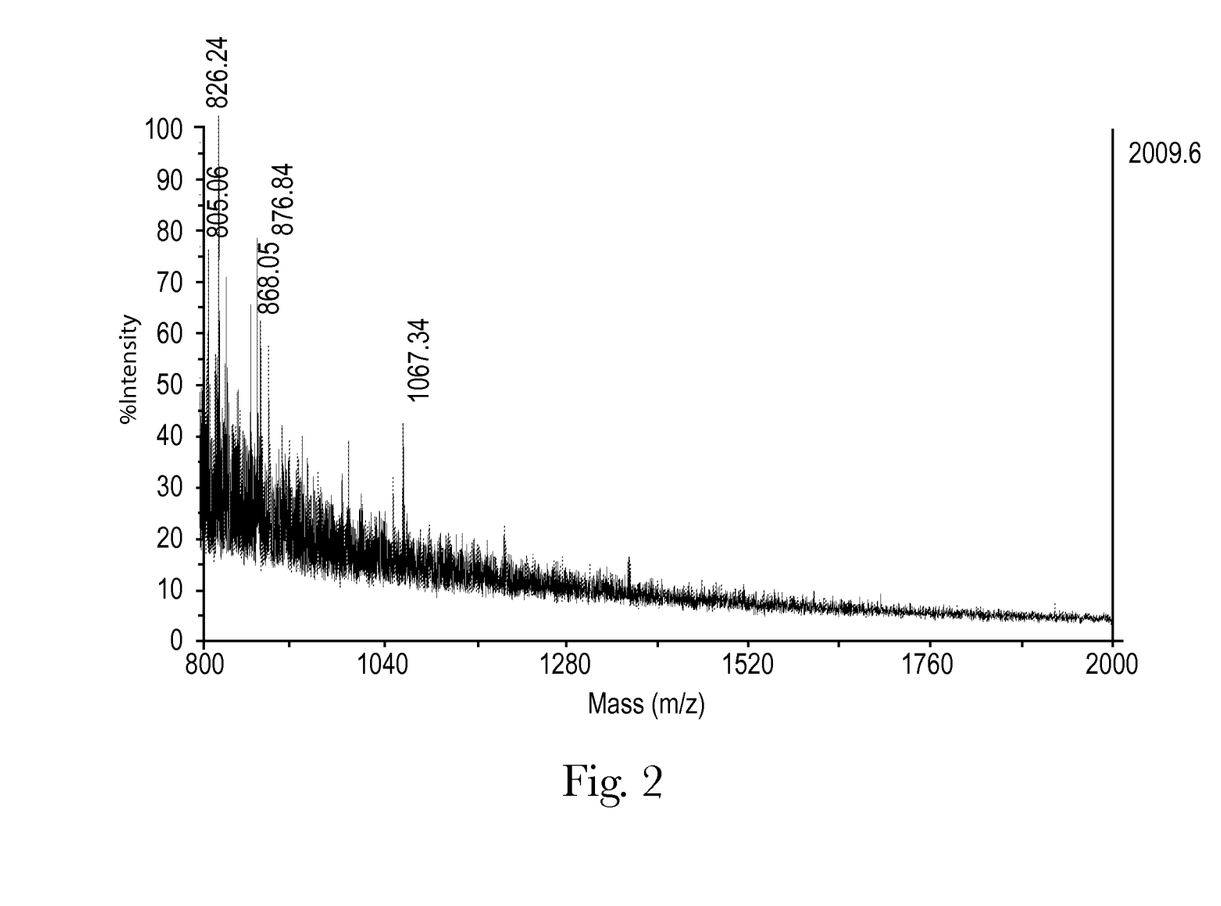
FIG. 2. MALDI mass spectrum of extracts from virgin hair samples with heat treatment, demonstrating the presence of the m/z 1067 biomarker peak.
Figure 3:
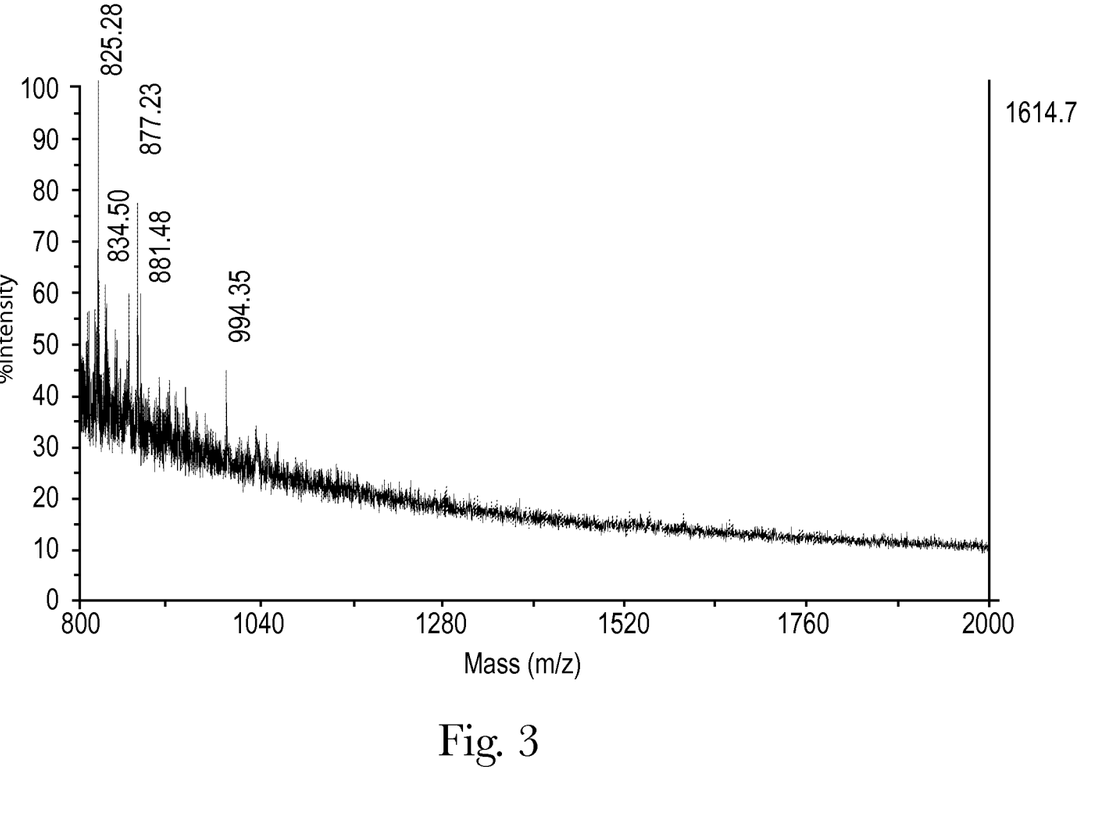
FIG. 3. MALDI mass spectrum of extracts from bleached hair samples without heat treatment.

A bleaching solution is placed in a tall beaker and the swatches are hung into the bleaching solution for 35 minutes.
   3. Rinsing—Swatches are rinsed by massaging the hair switch for the first 5 minutes under running water. Then the hair switches are continued rinsing under running water with no massaging for an additional 10 minutes.
   4. Drying—Excess water is squeezed out and hair switch is dried by towel. The hair switch is then dried with blow drier and brushing for 3 minutes.
   2) Heat Treatment of Hair to Generate Marker Peptides which Indicate Damage from Heat Treatments:
Hair samples are exposed to heat using the following protocols:
Virgin Hair and Bleached curly hair are treated with 3 different types of heat at 3 cycle levels. (3 types of heat, blow dryer, 350 F flat iron, 450 F flat iron); 3 cycle levels 1 treatment, 5 treatments, 10 treatments
Blow Dryer Heat Procedure.
1. Hair is placed in a Hot blow dryer box at 150 F for 10 minutes.
2. Hair is then removed and allowed to cool for 10 minutes.
3. This is repeated for 1, 5, and 10 cycles.
Flat Iron Procedure.
1. Hair is either treated with a 350 F or 450 F flat iron.
2. Hair is pressed with a flat iron from root to tip for 8 passes, this is equal to 1 cycle.
3. Hair is then allowed to cool for 10 min.
4. This is repeated for 1, 5 and 10 cycles.
   3) Hair Tresses Preparation Post Heat Treatment:
   The amount of overall peptide damage sustained by the hair tresses as a result of the heat treatments is assessed by measuring total peptide loss from the hair. Briefly, 0.2-0.3 g of hair from each tress is clipped into 2 inch segments and added to a glass scintillation vial. Deionized (DI) water is added at a ratio of 1.0 ml DI water to 0.1 g hair, and samples are subjected to physical agitation for 60 minutes at 2,500 rpm on a vortex platform. Water extracts are analyzed for total protein concentration using the Lowry protein quantification assay.
   4) MALDI-TOF Analysis of Hair Tresses Post Heat Treatment:
   The specific peptide damage sustained by the hair tresses as a result of the heat treatments is determined by analyzing the water extracts described above by MALDI-TOF analysis. Water extracts are mixed (1:1) directly with a MALDI matrix solution (10 mg of α-Cyano-4-hydroxycinnamic acid (CHCA) dissolved in 1 ml of 80:20:0.1 acetonitrile: water: trifluoroacetic acid). About 1 ul each sample is spotted on the MALDI plate and analyzed by MALDI-TOF/TOF 4800 plus system (AB-Sciex). A peak is found at m/z 1061 for bleached hair, and another peak at m/z 1067 for virgin hair.
   FIG. 1 is a MALDI mass spectrum of extracts from virgin hair samples without heat treatment.
   Matrix-assisted laser desorption ionization time-of-flight (MALDI-TOF) mass spectrometry is used to detect peptide marker ions from the water extracts. 5 ul of the water extracts from virgin hair without heat treatment are mixed 5 ul MALDI matrix α-cyano-4-hydroxycinnamic acid (α-cyano-4-hydroxycinnamic acid at 10 mg/ml in 80% acetonitrile/water/0.1% trifluroacetic acid). 0.7 microliter of this mixture is spotted on a target plate and allowed to air dry at room temperature before MALDI analysis. A MALDI TOF/TOF 4800 Plus Mass Analyzer (AB-Sciex, Framingham, Mass., U.S.A.) is used in the positive ion reflectron mode. The mass spectrometer uses a 200-Hz frequency Nd:YAG laser, operating at a wavelength of 355 nm. Ions generated by the MALDI process are accelerated at 20 kV. For each spot, 250 shots per subspectra with 2500 total shots per spectrum. MALDI-TOF mass spectra is generated typically in the mass range 800-4000 Da. Laser intensity is set between 4000 and 4500 V. Data is collected in an automated fashion using random sampling over the sample spot.
   FIG. 1 demonstrates a typical MALDI spectrum for untreated virgin hair.
   FIG. 2 is a MALDI mass spectrum of extracts from virgin hair samples with heat treatment, demonstrating the presence of m/z 1067 biomarker peak.
   Matrix-assisted laser desorption ionization time-of-flight (MALDI-TOF) mass spectrometry is used to detect peptide marker ions from the water extracts. 5 ul of the water extracts from virgin hair samples with heat treatment are mixed 5 ul MALDI matrix α-cyano-4-hydroxycinnamic acid (α-cyano-4-hydroxycinnamic acid at 10 mg/ml in 80% acetonitrile/water/0.1% trifluroacetic acid). 0.7 microliter of this mixture is spotted on a target plate and allowed to air dry at room temperature before MALDI analysis. A MALDI TOF/TOF 4800 Plus Mass Analyzer (AB-Sciex, Framingham, Mass., U.S.A.) is used in the positive ion reflectron mode. The mass spectrometer uses a 200-Hz frequency Nd:YAG laser, operating at a wavelength of 355 nm. Ions generated by the MALDI process is accelerated at 20 kV. For each spot, 250 shots per subspectra with 2500 total shots per spectrum. MALDI-TOF mass spectra is generated typically in the mass range 800-4000 Da. Laser intensity is set between 4000 and 4500 V. Data is collected in an automated fashion using random sampling over the sample spot. The intensity of peptide marker peaks for each extract is measured for quantitation.
   FIG. 2 demonstrates virgin hair that has been subject to repeated heat damage from 450 F flat iron. In FIG. 2 a signal appears at m/z 1067 which is not present in the untreated virgin hair sample.
   FIG. 3 is a MALDI mass spectrum of extracts from bleached hair samples without heat treatment.
   Matrix-assisted laser desorption ionization time-of-flight (MALDI-TOF) mass spectrometry is used to detect peptide marker ions from the water extracts. 5 ul of the water extracts from bleached hair samples without heat treatment are mixed 5 ul MALDI matrix α-cyano-4-hydroxycinnamic acid (α-cyano-4-hydroxycinnamic acid at 10 mg/ml in 80% acetonitrile/water/0.1% trifluroacetic acid). 0.7 microliter of this mixture is spotted on a target plate and allowed to air dry at room temperature before MALDI analysis. A MALDI TOF/TOF 4800 Plus Mass Analyzer (AB-Sciex, Framingham, Mass., U.S.A.) is used in the positive ion reflectron mode. The mass spectrometer uses a 200-Hz frequency Nd:YAG laser, operating at a wavelength of 355 nm. Ions generated by the MALDI process are accelerated at 20 kV. For each spot, 250 shots per subspectra with 2500 total shots per spectrum. MALDI-TOF mass spectra is generated typically in the mass range 800-4000 Da. Laser intensity is set between 4000 and 4500 V. Data is collected in an automated fashion using random sampling over the sample spot.

FIG. 3 demonstrates a typical MALDI spectrum for bleached hair.

Figure 4:
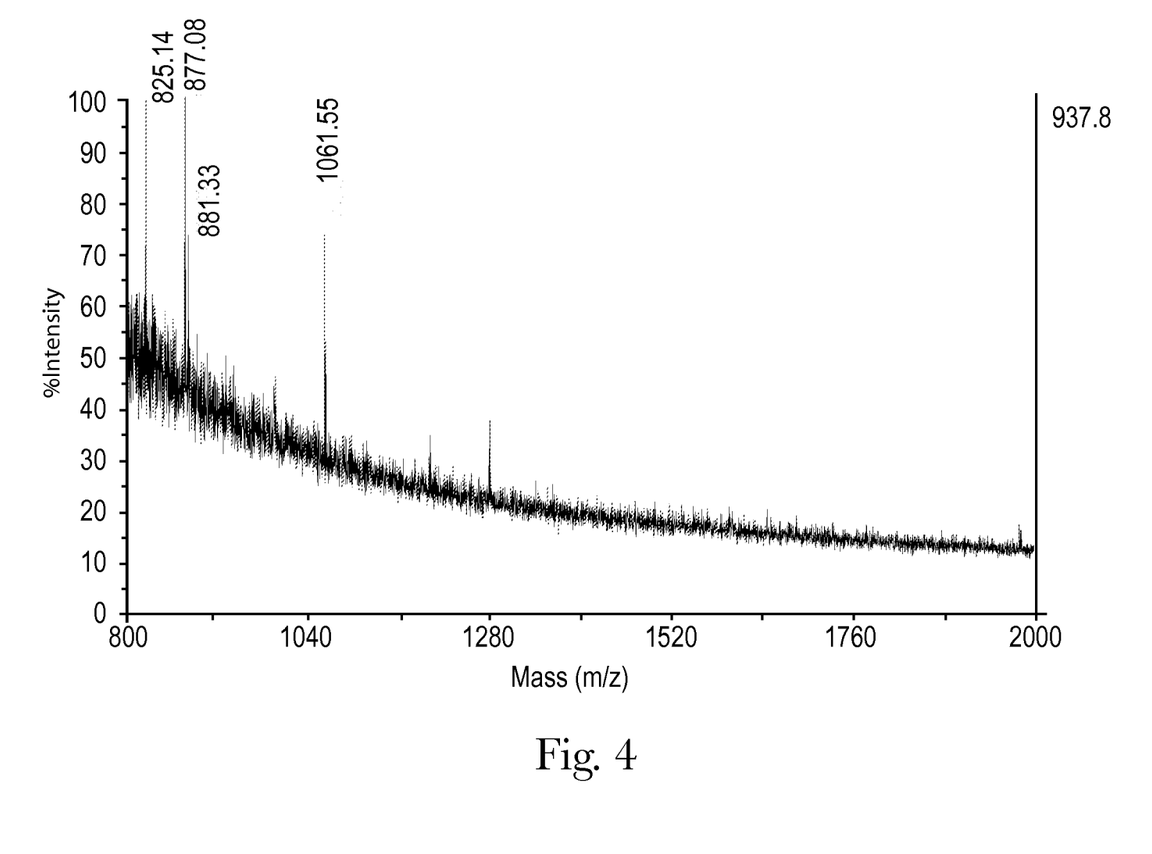
FIG. 4. MALDI mass spectrum of extracts from bleached hair samples with heat treatment, demonstrating the presence of m/z 1061 peptide biomarker peak.

FIG. 4 is a MALDI-TOF spectrum of extracts from bleached hair with heat treatment, demonstrating the presence of m/z 1061 peptide biomarker peak.

Matrix-assisted laser desorption ionization time-of-flight (MALDI-TOF) mass spectrometry is used to detect peptide marker ions from the water extracts. 5 ul of the water extracts from bleached hair samples with heat treatment are mixed 5 ul MALDI matrix α-cyano-4-hydroxycinnamic acid (α-cyano-4-hydroxycinnamic acid at 10 mg/ml in 80% acetonitrile/water/0.1% trifluroacetic acid). 0.7 microliter of this mixture is spotted on a target plate and allowed to air dry at room temperature before MALDI analysis. A MALDI TOF/TOF 4800 Plus Mass Analyzer (AB-Sciex, Framingham, Mass., U.S.A.) is used in the positive ion reflectron mode. The mass spectrometer uses a 200-Hz frequency Nd:YAG laser, operating at a wavelength of 355 nm. Ions generated by the MALDI process are accelerated at 20 kV. For each spot, 250 shots per subspectra with 2500 total shots per spectrum. MALDI-TOF mass spectra is generated typically in the mass range 800-4000 Da. Laser intensity is set between 4000 and 4500 V. Data is collected in an automated fashion using random sampling over the sample spot. The intensity of peptide marker peaks for each extract is measured for quantitation.

FIG. 4 demonstrates bleached hair that has been subject to repeated heat damage from 450 F flat iron. In FIG. 4, a signal appears at m/z 1061 which is not present in the non-heat treated bleach hair sample.

EXAMPLE B

1. MALDI-TOF Analysis of Hair Tresses Post-Heat Treatment:

The specific peptide damage sustained by the hair tresses as a result of the heat exposure is determined by analyzing the water extracts described above by MALDI-TOF analysis. Water extracts are mixed (1:1) directly with a MALDI matrix solution (10 mg of α-Cyano-4-hydroxycinnamic acid (CHCA) dissolved in 1 ml of 80:20:0.1 acetonitrile: water: trifluoroacetic acid). About 1 ul each sample is spotted on the MALDI plate and analyzed by MALDI-TOF/TOF 4800 plus system (AB-Sciex). A peptide marker for hair damage from heat treatment is detected in the water extracts with m/z 1061 for bleached hair and 1067 for virgin hair. This marker is also found to increase as a function of the amount of heat exposure to the hair within a consumer-relevant exposure range (Table 1).

TABLE 1

| Hair Type | Treatment | m/z 1067 | m/z 1061 |
|---|---|---|---|
| Virgin Hair | Untreated | 1125 | |
| Virgin Hair | Blow Dry Box 1 Cycle 150° F. | 1041 | |
| Virgin Hair | Blow Dry Box 5 Cycle 150° F. | 7655 | |
| Virgin Hair | Blow Dry Box 10 Cycle 150° F. | 5184 | |
| Virgin Hair | Flat Iron 1 Cycle 350° F. | 6567 | |
| Virgin Hair | Flat Iron 5 Cycle 350° F. | 7463 | |
| Virgin Hair | Flat Iron 10 Cycle 350° F. | 7100 | |
| Virgin Hair | Flat Iron 1 Cycle 450° F. | 4876 | |
| Virgin Hair | Flat Iron 5 Cycle 450° F. | 7185 | |
| Virgin Hair | Flat Iron 10 Cycle 450° F. | 5726 | |
| Bleached Hair | Untreated | | 1263 |
| Bleached Hair | Blow Dry Box 1 Cycle 150° F. | | 1145 |
| Bleached Hair | Blow Dry Box 5 Cycle 150° F. | | 1041 |
| Bleached Hair | Blow Dry Box 10 Cycle 150° F. | | 2318 |
| Bleached Hair | Flat Iron 1 Cycle 350° F. | | 1969 |
| Bleached Hair | Flat Iron 5 Cycle 350° F. | | 2135 |
| Bleached Hair | Flat Iron 10 Cycle 350° F. | | 1872 |
| Bleached Hair | Flat Iron 1 Cycle 450° F. | | 1417 |
| Bleached Hair | Flat Iron 5 Cycle 450° F. | | 2030 |
| Bleached Hair | Flat Iron 10 Cycle 450° F. | | 2480 |

Treatment with Crosslinking Agent:
1. Prewash hair.
2. Apply 2.0 ml of treatment with combing to distribute evenly.
3. Leave on 30 minutes to develop.
4. Blow dry with brushing.
5. Flat iron at 450° F. with combing to remove tangles.

Heat Only Treated Hair
1. Prewash hair.
2. Blow dry with brushing.
3. Flat iron at 450° F. with combing to remove tangles.

Figure 5:
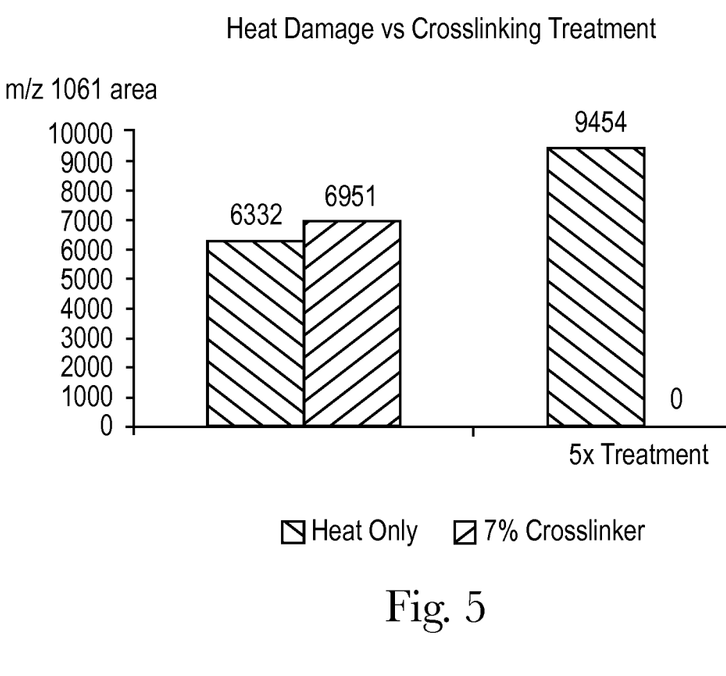
FIG. 5. A graph demonstrating heat protective effects of crosslinking treatment.

FIG. 5—As hair is exposed to 5 cycles of heat treatment, the result is an increase in the marker intensity. However, in the sample that has been treated with 7.5% glyoxylic acid (a crosslinking treatment) and heat, the marker m/z 1061 is no longer present, indicating less damage from heat.

However, it has also been shown that pretreatment with a peptide crosslinking agent results in reduction of the level of damage, as shown by the heat damage biomarker, which is reduced. In addition, pretreatment of the hair with heat protection compositions can also reduce heat damage to the hair.

Crosslinking Composition

One method of mitigating heat damage comprises applying a crosslinking composition to keratin fibres, wherein the crosslinking composition comprises a crosslinking agent, wherein the crosslinking agent has at least one functional groups selected from the group consisting of: —NH$_2$, —NH—, —SH, —OH, —C(=O)H, —C=O, and COOH; and wherein the crosslinking agent has a molecular weight of 500 g/mol or less. In at least one embodiment, the crosslinking agent has a molecular weight of 400 g/mol or less. In at least one embodiment, the crosslinking agent has a molecular weight of 300 g/mol or less, or from about 50 g/mol to 250 g/mol, or from about 80 g/mol to about 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle.

In at least one embodiment, the crosslinking agent is liquid at 25° C. Crosslinking agents being liquid at this temperature have the advantage of providing improved hair feel versus crosslinking agents that are solid at this temperature.

In at least one embodiment, the crosslinking agent is capable of crosslinking keratin. In at least one embodiment, the crosslinking agent is selected from the group consisting of: diols, carboxylic acids, amines, diamines, reducing sugars, carbonyls, carboxylic acids, and mixtures thereof. In at least one embodiment, the crosslinking agent comprises at least one reactive sites selected from the functional groups consisting of: aldehyde, hydroxyl, carboxyl, and combinations thereof. In at least one embodiment, the crosslinking agent is selected from the group consisting of: 1,7-diaminoheptane, 1,4-diaminobutane, 6-aminohexan-1-ol, 6-amino hexanoic acid, 2-aminoacetic acid, 2-amino-2-oxo-ethanoic acid, 4-aminobutanoic acid, ribose, arabinose, xylose, lyxose, galactose, mannose, 3-(2-hydroxyethyl)-2-oxazolidinone, hexane-2,5-dione, butane-2,3-dione, ethanedial, 2-hydroxy-butanedial, 4-oxo-pentanoic acid, 1,4-butanediol, 1,6-hexanediol, 1,2,4-butanetriol, 1,2,6-hexanetriol, butanedioic acid, heptanedioic acid, oxoethanoic acid, 2,2-dihydroxyethanoic acid, 2,2'-oxybis(2-hydroxy)-ethanoic acid, 2-hydroxypropane-1,2,3-tricarboxylic acid, 1,2,3,4-butanetetracarboxylic acid, 1,3-dioxolan-2-one, dimethyl carbonate, diethyl carbonate, diphenyl carbonate; 1,3-dioxan-2-one, 4-methyl-1,3-dioxolan-2-one, and mixtures thereof. In at least one embodiment, the crosslinking agent is selected from the group consisting of: ribose, arabinose, oxoethanoic acid, 2,2-dihydroxyethanoic acid, 2-hydroxypropane-1,2,3-tricarboxylic acid, 1,2,3,4-butanetetracarboxylic acid, 1,3-dioxolan-2-one, and mixtures thereof.

In at least one embodiment, the crosslinking composition comprises from about 0.1% to about 40% crosslinking agent. In at least one embodiment, the composition comprises from about 1% to about 20%, or from about 0.1% to about 15%, or from about 1% to about 12%, or from about 2% to about 10% crosslinking agent.

In at least one embodiment, the crosslinking composition comprises an crosslinking agent, wherein the crosslinking agent is an amine or diamine. Amines are useful because they are often naturally-derived (e.g. glycine), which is preferred by consumers versus synthetic compounds. This is not only for perceived health and lack of sensitisation reasons, but also for sustainability and environmental reasons—amines usually break down naturally and quickly and do not require special disposal methods. Also, amines are normally liquid at 25° C., which is useful from a feel perspective—consumers when touching their keratin fibres feel reduced roughness and friction versus actives being solid at 25° C. In at least one embodiment, the crosslinking agent is liquid at 25° C. The crosslinking agent is an amine or diamine; wherein the crosslinking agent has at least two functional groups selected from the group consisting of: —NH$_2$, —NH—, —SH, —OH, —C($=$O)H, —C$=$O, —SH, and COOH; and wherein the crosslinking agent has a molecular weight of 500 g/mol or less. In at least one embodiment, the crosslinking agent has a molecular weight of 400 g/mol or less, or 300 g/mol or less, or from about 50 g/mol to 250 g/mol, or from about 80 g/mol to about 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle.

In at least one embodiment, the crosslinking agent is a primary or secondary amine. Amines usually include an organic species bearing at least one nitrogen atom as part of a functional group. Amines may be mono-amines bearing one functional group comprising at least one nitrogen atom, diamines bearing two functional groups each comprising at least one nitrogen atom or polyamines bearing more than two functional groups each comprising at least one nitrogen atom. In a primary amine the nitrogen atom bears two hydrogen atoms and one organic moiety. In a secondary amine in which the nitrogen atom bears one hydrogen atoms and two organic moieties. In at least one embodiment, the organic moiety or moieties is/are independently selected from the group consisting of: $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ hydroxy, $C_1$-$C_{32}$ alkoxy, $C_1$-$C_{32}$ substituted alkoxy, $C_1$-$C_{32}$ alkylamino, and $C_1$-$C_{32}$ substituted alkylamino, —OH, —NH$_2$, and $=$NH.

In at least one embodiment, the crosslinking agent comprises at least one further functional group. In at least one embodiment, the further functional group is any organic moiety comprising at least one of an Oxygen, Nitrogen, Phosphorous, Boron or Sulfur atom. In at least one embodiment, the further functional group is selected from the group consisting of: Hydroxyl, Carbonyl, Aldehyde, Haloformyl, Carbonate ester, Carboxylate, Carboxyl, Ester, Methoxy, Hydroperoxy, Peroxy, Ether, Hemiacetal, Hemiketal, Acetal, Ketal, Orthoester, Orthocarbonate ester, Carboxamide, Primary amine, Secondary amine, Tertiary amine, Ammonium, Primary ketimine, Secondary ketimine, Primary aldimine, Secondary aldimine, Imide, Azide, Azo or Diimide, Cyanate, Isocyanate, Nitrate, Nitrile, Isonitrile, Nitrosooxy, Nitro, Nitroso, Pyridyl, Sulfhydryl, Sulfide, Disulfide, Sulfinyl, Sulfonyl, Sulfino, Sulfo, Thiocyanate, Isothiocyanate, Carbonothioyl, Carbonothioyl, Phosphino, Phosphono, Phosphate, Borono, Boronate, Borino, Borinate. In at least one embodiment, the crosslinking agent is a polyamine.

In at least one embodiment, the crosslinking agent is a diamine. In at least one embodiment, the crosslinking agent is a diamine conforming to the formula H$_2$N—(CH$_2$)n-NH$_2$, wherein n is an integer from 3 to 12, and isomers thereof. In at least one embodiment, the crosslinking agent is a diamine conforming to the formula H$_2$N—(CH$_2$)n-NH$_2$, wherein n is an integer from 2 to 12, or from 4 to 10, or from 5 to 8, and isomers thereof. 2-methylpropane-1,3-diamine is isomer of 1,4-diaminobutane. In at least one embodiment, the crosslinking agent is selected from the group consisting of: 1,7-diaminoheptane, 1,4-diaminobutane, 6-aminohexan-1-ol, 6-amino hexanoic acid, 2-aminoacetic acid, 2-amino-2-oxo-ethanoic acid, 4-aminobutanoic acid, and mixtures thereof. In at least one embodiment, the crosslinking agent is a diamine and wherein the diamine is selected from the group consisting of: 1,2-diaminoethane, 1,3-diaminopropane, 2-methylpropane-1,3-diamine, 1,4-diaminobutane, 1,5-diaminopentane, 1,6-diaminohexane, 1,7-diaminoheptane, 1,8-diaminooctane, 1,9-diaminononane, 1,10-diaminodecane, and mixtures thereof. In at least one embodiment, the crosslinking agent is a diamine and wherein the diamine is selected from the group consisting of: 1,7-diaminoheptane, 1,4-diaminobutane, and mixtures thereof. 1,4-diaminobutane has a molecular weight of about 88 g/mol and 1,7-diaminoheptane has a molecular weight of about 130 g/mol. In at least one embodiment, the crosslinking agent comprises a thiol group. In at least one embodiment, the crosslinking agent is 2-aminoethanethiol.

In at least one embodiment, the crosslinking agent is a sugar. Sugars are useful because they are naturally-derived, which is preferred by consumers versus synthetic compounds. This is not only for perceived health and lack of sensitisation reasons, but also for sustainability and environmental reasons—sugars break down naturally and quickly and do not require special disposal methods. Furthermore, sugars are also easy to source and relatively inexpensive. The crosslinking agent has a molecular weight of 500 g/mol or less. In at least one embodiment, the crosslinking agent has a molecular weight of 300 g/mol or less, or from about 50 g/mol to 250 g/mol, or from about 80 g/mol to about 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle. In at least one embodiment, the crosslinking agent is liquid at 25° C. Crosslinking agents being liquid at this temperature have the advantage of providing improved hair feel versus crosslinking agents that are solid at this temperature. In at least one embodiment, the crosslinking agent is a monosaccharide. In at least one embodiment, the sugar is a monosaccharide and wherein the crosslinking composition comprises from about 0.1% to about 40%, or from about 0.5% to about 20%, or from about 1% to about 15%, or from about 7% to about 20%, or from about 8% to about 19%, or from about 10% to about 18% monosaccharide. In at least one embodiment, the crosslinking agent is a pentose or a hexose.

In at least one embodiment, the crosslinking composition comprises a reducing sugar, where the crosslinking composition is heated to a temperature of 100° C., the composition comprises from about 1% to about 20% reducing sugar. In at least one embodiment, the crosslinking composition comprises a reducing sugar and wherein, where the crosslinking composition is heated to a temperature of 100° C., the crosslinking composition comprises from about 12% to about 18% reducing sugar. In at least one embodiment, the crosslinking composition comprises sucrose, a buffering agent and a cosmetically acceptable carrier; and wherein, where the crosslinking composition is heated to a temperature of 100° C., the crosslinking composition comprises from about 1% to about 20% reducing sugar. Sucrose is able to break down into reducing sugar following heating. In at least one embodiment, the crosslinking composition comprises a reducing sugar. In at least one embodiment, the crosslinking composition comprises from about 0.1% to about 20.0%, or from about 2% to about 15%, or from about 5% to about 12% reducing sugar. In at least one embodiment, the crosslinking composition comprises from about 12% to about 18% reducing sugar. In at least one embodiment, the crosslinking composition comprises a total amount of reducing sugar being from about 12% to about 18% reducing sugar.

In at least one embodiment, the crosslinking composition comprises a reducing sugar and a cosmetically acceptable carrier. As used herein, the expression "reducing sugar" means any sugar that either has an aldehyde group or is capable of forming an aldehyde group in solution through isomerism, and that gives a positive result in the Benedict's test. An aldehyde group is —C(=O)H. The Benedict's test involves employment of the Benedict's solution. The Benedict's solution is available from Aldrich as 'Benedict's Reagent', which comprises sodium carbonate, copper sulphate pentahydrate and 2,5-difluorotoluene. In the Benedict's test, 1 mL of Benedict's solution is added to a 20 mL of 5% aqueous solution comprising a dissolved test compound. Benedict's solution contains blue copper(II) ions ($Cu^{2+}$). The solution is heated to 80° C. for 15 min and the resulting colour change is noted. The cupric ion of the Benedict's solution is reduced to cuprous ion by the aldehyde of the sugar. A positive test is confirmed with a change in colour as cupric ions ($Cu^{2+}$) are converted to cuprous ions i.e. reduced to copper(I) ions ($Cu^+$). These are precipitated as red copper(I) oxide which is insoluble in water. The test is also designed for longer heating time and higher temperature to note any colour change. The solution may range in colour (with increasing amounts of reducing sugar) from green, through yellow and orange, to red. Any colour change away from blue suggest levels of reducing sugar. The wavelength will change with the colour.

TABLE 2

Assessment of sugars using the Benedict's Test

| Sugar | 80° C., 15 min | 100° C., 40 min |
|---|---|---|
| Control (buffer solution*) | Negative | Negative |
| Ribose | Positive | Positive |
| Arabinose | Positive | Positive |
| Glucose | Positive | Positive |
| Fructose | Positive | Positive |
| Xylose | Positive | Positive |
| Sucrose | Negative | Positive |
| Methyl glucoside | Negative | Positive |

*Benedict's solution only.

In general, the Benedict's reagent is used as a test for the presence of reducing sugars. This includes all monosaccharides and many disaccharides, including lactose and maltose. Even more generally, Benedict's test will detect the presence of aldehydes, and alpha-hydroxy-ketones, including those that occur in certain ketoses. Thus, although fructose, a ketose, is not strictly a reducing sugar, it is an alpha-hydroxy-ketone, it gives a positive test because it is converted to the aldoses glucose and mannose by the base in the reagent. The copper sulphate in Benedict's solution reacts with reducing sugars. One liter of Benedict's reagent can be prepared from 100 g of anhydrous sodium carbonate, 173 g of sodium citrate and 17.3 g of copper(II) sulfate pentahydrate. Benedict's Reagent provides a quantitative test for reducing sugars along with qualitative test. The colour of the obtained precipitate gives an idea about the quantity of sugar present in the solution. A greenish precipitate indicates about 0.5% concentration; yellow precipitate indicates 1% concentration; orange indicates 1.5% and red indicates 2% or higher concentration. A positive result in the Benedict's test can be recognised for a compound by a 5% (weight/weight) solution of compound in water as a red colouring. The aldehyde group of the sugar allows the sugar to act as a reducing agent, for example in the Benedict's test.

In at least one embodiment, the reducing sugar is selected from the group consisting of: ribose, arabinose, xylose, lyxose, galactose, mannose, and mixtures thereof. In at least one embodiment, the reducing sugar is either ribose, arabinose, or a mixture thereof. In at least one embodiment, the crosslinking composition comprises a reducing sugar and wherein the reducing sugar is selected from the group consisting of: arabinose, ribose, and mixtures thereof. In at least one embodiment, the sole reducing sugar is a pentose. In at least one embodiment, the sole reducing sugar is selected from the group consisting of: arabinose, ribose, and mixtures thereof. The reducing sugars arabinose, ribose, and mixtures thereof have the benefit of excellent straightening performance. By treating hair with reducing sugar and subsequent heat treatment as per the invention the treated hair becomes durably straight. Arabinose and ribose are 5 carbon sugars and these are found to have even better performance than sugars with other carbon numbers, such as 6 carbon and 7 carbon sugars. On the other hand, 6 carbon sugars are highly available and thus have economic advantages. In at least one embodiment, the crosslinking composition comprises a total amount of reducing sugar being from about 12% to about 18% reducing sugar, and wherein the crosslinking composition comprises arabinose.

In at least one embodiment, the crosslinking agent comprises a functional group selected from the group consisting of: —C(=O)—, —C(=O)—H, and —C(=O)—O—. In at least one embodiment, the crosslinking agent comprises at least one functional groups functional group selected from the group consisting of: —C(═O)—, —C(═O)—H, —OH, —NH$_2$, and —C(═O)—O—. In at least one embodiment, the crosslinking agent comprises at least one functional groups functional group selected from the group consisting of: —C(═O)—H, —OH, —NH$_2$. In at least one embodiment, the crosslinking agent is a carbonyl compound. In at least one embodiment, the crosslinking agent is an aldehyde. Aldehydes are useful in that they react with amino groups in keratin fibers. Since keratin fibers are polypeptides, available amino groups are common.

In at least one embodiment, the crosslinking agent conforms to the formula H$_2$N—(CH$_2$)n-C(═O)—H, wherein n is an integer from 2 to 10, or from 5 to 8, and isomers thereof. In at least one embodiment, the crosslinking agent conforms to the formula H$_3$C—C(═O)—(CH$_2$)n-C(═O)—CH$_3$, wherein n is an integer from 0 to 10, from 1 to 8, or from 2 to 7, and isomers thereof. In at least one embodiment, the crosslinking agent comprises a heterocyclic 5-member ring. In at least one embodiment, the crosslinking agent comprises a heterocyclic 5-member ring comprising nitrogen and oxygen atoms. In at least one embodiment, the crosslinking agent is a ketone. In at least one embodiment, the crosslinking agent is a dial, or a dial having an OH group. In at least one embodiment, the crosslinking agent is an oxazolidone. In at least one embodiment, the crosslinking agent is selected from the group consisting of: 3-(2-hydroxyethyl)-2-oxazolidinone, hexane-2,5-dione, butane-2,3-dione, ethanedial, 2-hydroxy-butanedial, 4-oxo-pentanoic acid, isomers thereof, derivatives thereof, and mixtures thereof. In at least one embodiment, the crosslinking agent is selected from the group consisting of: 3-(2-hydroxyethyl)-2-oxazolidinone, hexane-2,5-dione, butane-2,3-dione, ethanedial, 2-hydroxy-butanedial, 4-oxo-pentanoic acid, and mixtures thereof. In at least one embodiment, the crosslinking agent is selected from the group consisting of: 3-(2-hydroxyethyl)-2-oxazolidinone, hexane-2,5-dione, butane-2,3-dione, 2-hydroxy-butanedial, and mixtures thereof. In at least one embodiment, the crosslinking agent is selected from the group consisting of: butane-2,3-dione; 2-hydroxy-butanedial; 2-hydroxy-butanedial; and mixtures thereof. In at least one embodiment, the crosslinking agent is selected from the group consisting of: butane-2,3-dione; 2-hydroxy-butanedial; and mixtures thereof.

Synthesis of Dialdehyde

To a solution of 1,2-O-isopropylidene-D-glucofuranose (50 grams, 0.227 mol, CAS#185-40-1, Sigma-Aldrich) in water (500 mL) in an ice bath is added solid sodium meta periodate (50 grams, 0.183 mol, CAS#7790-28-5, Aldrich) portion wise over 30 minutes. The reaction is warmed to room temperature and stirred for 24 hrs. Ethylene glycol (5 mL) is added and the reaction is stirred for 3 hr at room temperature. The solution is then lyophilized overnight to remove water. The residue is dissolved in water (100 mL) and then extracted with chloroform (3×500 mL). The organic layers are combined, dried (Mg$_2$SO$_4$) and then the solvent is removed in vacuo to give a gummy, viscous oil. The gum is dissolved in water (200 mL), and treated with Amberlite H+ resin (5 grams) at 70-80° C. for about 24 hrs. The reaction is cooled to room temperature, the resin is filtered off, and the filtrate is lyophilized to remove the water. The resulting off-white solid is stored in the freezer at 0° C. until testing.

Amberlite H+ Resin can be Obtained Rohm and Haas

In at least one embodiment, the crosslinking agent comprises at least two functional groups selected from: —C(OH)— and —C(═O)OH. In at least one embodiment, the crosslinking agent is selected from the group consisting of: 1,2,4-butanetriol, oxobutanedioic acid, butanedioic acid, heptanedioic acid, 1,4-butanediol, 1,6-hexanediol, 1,2,6-hexanetriol, 6-amino-1-hexanol, 6-aminohexanoic acid, 2-aminobutanoic acid, ethane-1,2-diol, aminoethanoic acid, 2-hydroxyethanoic acid, 4-oxopentanoic acid, ethanedioic acid, aminooxoethanoic acid, and mixtures thereof. In at least one embodiment, the crosslinking agent is a diol conforming to the formula HO—(CH$_2$)n-OH, wherein n is an integer from 2 to 12, or isomers thereof. In at least one embodiment, the crosslinking agent is a triol.

In at least one embodiment, the crosslinking agent comprises a —C(═O)OH functional group. Said carboxylic acid group has the advantage that the reaction with OH groups the kertain polypeptide is a more efficient reaction than other chemistries. In at least one embodiment, the crosslinking agent comprises a hydroxyl functional group. The hydroxyl group has the advantage that the crosslinking agent can further provide conditioning to the keratin fibres. In at least one embodiment, the crosslinking agent comprises both a —C(OH)— and a —C(═O)OH functional group. In at least one embodiment, the crosslinking agent conforms to the formula HO—(CH$_2$)n-COOH, wherein n is an integer from 2 to 12, or from 4 to 10, or from 5 to 8, or isomers thereof. In at least one embodiment, the crosslinking agent conforms to the formula HOOC—(CH$_2$)n-COOH, wherein n is an integer from 2 to 12, or from 4 to 10, or from 5 to 8, or isomers thereof. In at least one embodiment, the crosslinking agent is selected from the group consisting of: 1,4-butanediol, 1,6-hexanediol, 1,2,4-butanetriol, 1,2,6-hexanetriol, butanedioic acid, heptanedioic acid, and mixtures thereof. In at least one embodiment, the crosslinking agent further comprises a functional group selected from the group consisting of: —NH$_2$ and —C(═O)—. In at least one embodiment, the crosslinking agent is a triol and has 4 or more carbon atoms. In at least one embodiment, the crosslinking composition is substantially free of 2-hydroxypropane-1,2,3-tricarboxylic acid and propane-1,2,3-triol.

In at least one embodiment, the crosslinking agent is selected from the group consisting of: 1,4-butanediol, 1,6-hexanediol, 1,2,4-butanetriol, 1,2,6-hexanetriol, butanedioic acid, heptanedioic acid, 2-oxo-butanedioic acid, 6-amino-1-hexanol, 6-amino hexanoic acid, 2-aminobutanoic acid, 1,2-ethanediol, 2-aminoacetic acid, 2-hydroxy-acetic acid, 4-oxo-pentanoic acid, ethanedioic acid, 2-amino-2-oxo-acetic acid, and mixtures thereof. In at least one embodiment, the crosslinking agent is selected from the group consisting of: 1,2,4-butanetriol; oxobutanedioic acid; butanedioic acid;

heptanedioic acid; 1,4-butanediol; 1,6-hexanediol; 1,2,6-hexanetriol; and mixtures thereof.

In at least one embodiment, the crosslinking agent is selected from the group consisting of: oxoethanoic acid, 2,2-dihydroxyethanoic acid, 2,2'-oxybis(2-hydroxy)-ethanoic acid, a derivative thereof, and mixtures thereof. In at least one embodiment, the crosslinking agent is 2,2-dihydroxyethanoic acid. In at least one embodiment, the active is a derivative of oxoethanoic acid, 2,2-dihydroxyethanoic acid, or 2,2'-oxybis(2-hydroxy)-ethanoic acid. Suitable derivatives are disclosed in WO2013/117771A1, which is incorporated herein by reference. In at least one embodiment, the active is a salt of oxoethanoic acid, 2,2-dihydroxyethanoic acid, 2,2'-oxybis(2-hydroxy)-ethanoic acid, or a mixture of two or more of said salts. In at least one embodiment, the derivative is selected from the group consisting of: methyl glyoxylate, ethyl glyoxylate, 2-hydroxyethyl glyoxylate, 3-hydroxypropyl glyoxylate, glyceryl glyoxylate, dihydroxyacetone glyoxylate, glyceryl diglyoxylate or triglyoxylate, sorbitol mono-, di- or triglyoxylate, glucose mono-, di- or triglyoxylate, 1,3-propanediol glyoxylate, 1,2-ethanediol glyoxylate, and mixtures thereof. In at least one embodiment, the derivative is selected from the group consisting of formulae 1 to 4 below, and mixtures thereof:

(1)

(2)

(3)

(4)

In at least one embodiment, the derivative is selected from the group consisting of formulae 1' to 6' below, and mixtures thereof:

(1')

(2')

(3')

(4')

(5')

(6')

In at least one embodiment, the derivative is selected from the group consisting of formulae 1" to 5" below, and mixtures thereof:

(1")

(2")

(3")

(4")

In at least one embodiment, the crosslinking agent is selected from the group consisting of: oxoethanoic acid, 2,2-dihydroxyethanoic acid, 2,2'-oxybis(2-hydroxy)-ethanoic acid, and mixtures thereof. In at least one embodiment, the crosslinking agent is a mixture of oxoethanoic acid, 2,2-dihydroxyethanoic acid, and 2,2'-oxybis(2-hydroxy)-ethanoic acid. In at least one embodiment, the crosslinking agent is 2,2-dihydroxyethanoic acid. Oxoethanoic acid and 2,2-dihydroxyethanoic acid are available from Sigma Aldrich.

In at least one embodiment, the crosslinking agent is selected from the group consisting of: 2-hydroxypropane-1,2,3-tricarboxylic acid, 1,2,3,4-butanetetracarboxylic acid, a derivative thereof, and mixtures thereof. In at least one embodiment, the crosslinking agent is 2-hydroxypropane-1,2,3-tricarboxylic acid. In at least one embodiment, the crosslinking agent is 1,2,3,4-butanetetracarboxylic acid. 2-hydroxypropane-1,2,3-tricarboxylic acid and 1,2,3,4-butanetetracarboxylic acid are available from Sigma Aldrich.

In at least one embodiment, the crosslinking agent is a carbonate ester. In at least one embodiment, the carbonate ester conforms to the formula $R_1O(C=O)OR_2$ wherein $R_1$ and $R_2$ are independently a $C_{1-18}$ alkyl, alkylene, or phenyl, which includes cyclic, non-cyclic, branched chain and straight chain. In at least one embodiment, the carbonate ester conforms to the formula $R_1O(C=O)OR_2$ wherein $R_1$ and $R_2$ are independently a $C_{1-10}$ alkyl or alkylene. In at least one embodiment, the carbonate ester conforms to the formula $R_1O(C=O)OR_2$ wherein $R_1$ and $R_2$ are independently selected from: methyl, ethyl, and phenyl. In at least one embodiment, the carbonate ester is selected from the group consisting of: 1,3-dioxolan-2-one; dimethyl carbonate; diethyl carbonate; diphenyl carbonate; 1,3-dioxan-2-one (trimethylene carbonate); 4-methyl-1,3-dioxolan-2-one; and mixtures thereof.

In at least one embodiment, the crosslinking composition has a pH of from about pH 2 to about pH 11. In at least one embodiment, the crosslinking composition has a pH of from about pH 2 to about pH 6.5, of from about pH 3 to about pH 5, or from about pH 3 to about pH 4. In at least one embodiment, the crosslinking composition has a pH of from about pH 6 to about pH 10. In at least one embodiment, the crosslinking composition has a pH of from about pH 6.5 to about pH 9.75, or from about pH 7.0 to about pH 9.5, or from about pH 7.5 to about pH 9.25, or from about pH 8.0 to about pH 9.0. In at least one embodiment, the crosslinking composition has a pH of from about pH 6.5 to about pH 9.75. A basic pH is useful in view of penetration into hair.

In at least one embodiment, the crosslinking composition comprises a buffering agent. In at least one embodiment, the buffering agent is a phosphate buffer. In at least one embodiment, the buffering agent is selected from the group consisting of: glycine/sodium hydroxide; sodium carbonate/sodium hydrogen carbonate, sodium tetraborate/sodium hydroxide; sodium bicarbonate/sodium hydroxide; ammonium chloride/ammonia.

In at least one embodiment, the crosslinking composition comprises an antioxidant. An antioxidant is useful in view of providing longer-term stability for the composition. In at least one embodiment, the crosslinking composition comprises from about 0.001% to about 5%, or from about 0.5% to about 1.0% antioxidant. Suitable antioxidants are described below.

In at least one embodiment, the crosslinking composition comprises a chelator or chelating agent. In at least one embodiment, the crosslinking composition comprises a safe and effective amount of a chelator or chelating agent. In at least one embodiment, the crosslinking composition comprises a chelating agent, and wherein the chelating agent is selected from the group consisting of: N-hydroxysuccinimide, EDTA, NTA, deferoxamine, hydroxamic acids and their salts, phytic acid, phytate, gluconic acid and its salts, transferrine, lactoferrin, histidine, ethylenediamine-N,N'-disuccinic acid and mixtures thereof. In a further embodiment, the crosslinking composition may compromise sugars, carbonyl containing compounds, carbonate esters. In at least one embodiment, the crosslinking composition comprises from about 0.00001% to about 10%, or from about 0.001% to about 5%, or from about 0.001% to about 5%, or from about 0.5% to about 1.0% chelating agent.

In at least one embodiment, the crosslinking composition comprises a hairstyling polymer. In at least one embodiment, the hairstyling polymer is selected from the group consisting of: non-ionic hairstyling polymer, anionic hairstyling polymer, zwitterionic and/or amphoretic hairstyling polymer, cationic hair styling polymer, or mixtures thereof. Suitable hairstyling polymers are described below.

Heat Protection Agents:

One means of mitigating heat damage may be through the use of a heat protection composition. Heat protection compositions, as used herein, refer to compositions that prevent or reduce damage either internally or externally to the keratin fiber caused from and external heat source. Typically external cuticle damage is graded visually using light microscopy and Scanning Electron Microscopy (SEM). Internal damage to keratin peptides indicated by a shift in the denaturation temperature is measured by Differential Scanning calorimietry (DSC) along with tensile and torsional property changes. Compositions claiming to provide heat protection typically increase the denaturation temperature of the hair peptide thereby reducing its level of damage upon treatment.

Suitable heat protection compositions can be hydrous or anhydrous and may comprise silicones, polymers, oils, quaternary ammonium compounds, glycols, humectants, metal salts, peptides, extracts, antioxidants, alpha hydroxy acids, hydrolyzed keratin and combinations thereof. Suitable silicones include but are not limited to: phenyltrimethicones, polydimethylsiloxane (PDMS), dimethicone, aminodimethicone and dimethicone crosspolymers. One or more silicones may be present at about 1% to about 95% by weight of the heat protection composition. Polymers include but are not limited to: polyvinylpyrrolidone (PVP), polyvinylalcohol (PVA), polyacrylates, polyurethanes, celluloses, polyquaterniums, and copolymers or mixtures thereof. One or more polymers may be present at about 1% to about 30% by weight of the heat protection composition.

Metal salts of aluminum, titanium, and zinc are also suitable for heat protection compositions. Non-limiting examples of metal salts include, but are not limited to: aluminum chloride, zinc chloride, titanium dioxide, and combinations thereof. One or more metal salts may be present in the heat protection composition at about 1% to about 10% by weight of the heat protection composition.

In a further embodiment, additional heat protection compositions may comprise the following: Oils, non-limiting examples such as Moroccan oil (argan oil), olive oil at about 0.5%-95%, emollient section of the Cosmetic Bench reference at about 0.5-95%; Quaternary ammonium compounds, non-limiting examples such as alkylbenzyldimethylammonium salts, alkyl betaines, hetercyclic ammonium salts, tetraalkylammonium salts at about 1-15%; Glycols, non-limiting examples such as ethylene, butylene, propylene glycol at about 1-50%; Humectants, non-limiting examples such as glycerin, sorbitol at about 1-25%; Peptides, non-limiting examples such as wheat peptides including amino acids at about 1-10%; Antioxidants, non-limiting examples such as seed oils, fruit, plant and nut derived components at about 0.5-95%; Cosmetic Bench Reference (reference) at about 1-30%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method to identify a treatment for heat damage of keratin fibers comprising
    a) applying a treatment composition to a hair sample A; applying no treatment composition to hair sample B, wherein sample A and sample B proceed from the same subject;
    b) applying heat to hair sample A and hair sample B;
    c) eluting a peptide from the hair samples with an aqueous solution;
    d) extracting the peptides using a suitable solvent sample;
    e) measuring a marker peptide by MALDI-MS, identified by m/z 1061 for bleached hair or m/z of 1067 for virgin hair, wherein sample A has a decrease in measured peptide compared to sample B.

2. The method of claim 1 wherein the treatment composition comprises a peptide cross linking agent.

3. The method of claim 2 wherein the peptide cross linking agent is selected from the group consisting of sugars, carbonate esters, amines, diamines, carbonyl containing compounds, carboxylic acids, oxyethanoic acids and mixtures thereof.

4. The method of claim 1 wherein the treatment composition comprises a heat protecting agent.

5. The method of claim 4 wherein the heat protecting agent is selected from the group consisting of silicones, polymers, glycols, humectants, metal salts, oils, hydrolyzed keratin and mixtures thereof.

* * * * *